(12) United States Patent
Kayser

(10) Patent No.: US 10,172,736 B1
(45) Date of Patent: Jan. 8, 2019

(54) COLOR-CODED BUCKLE STRAPS FOR A WHEELCHAIR

(71) Applicant: Becky Kayser, Fountain Hills, AZ (US)

(72) Inventor: Becky Kayser, Fountain Hills, AZ (US)

( * ) Notice: Subject to any disclaimer, the term of this patent is extended or adjusted under 35 U.S.C. 154(b) by 51 days.

(21) Appl. No.: 15/602,283

(22) Filed: May 23, 2017

(51) Int. Cl.
*A61G 5/12* (2006.01)
*A61F 5/37* (2006.01)

(52) U.S. Cl.
CPC ............ *A61F 5/3792* (2013.01); *A61G 5/122* (2016.11); *A61G 5/124* (2016.11); *A61G 5/128* (2016.11); *A61G 2205/20* (2013.01)

(58) Field of Classification Search
CPC ....... B60N 2/28; B60N 2/2884; B60N 2/2863
See application file for complete search history.

(56) References Cited

U.S. PATENT DOCUMENTS

| | | | |
|---|---|---|---|
| 3,768,862 A | 10/1973 | Williams | |
| D294,475 S | 3/1988 | Chen | |
| 4,913,490 A * | 4/1990 | Takahashi | B60N 2/2821 297/130 |
| 5,026,225 A | 6/1991 | McIntyre | |
| 5,052,750 A * | 10/1991 | Takahashi | B60N 2/2821 297/256.13 |
| 5,524,965 A * | 6/1996 | Barley | B60N 2/2827 297/252 |
| 5,697,329 A | 12/1997 | Bell | |
| 5,845,372 A * | 12/1998 | Smith | B60N 2/2806 24/168 |
| 5,896,859 A | 4/1999 | Carroll | |
| 6,289,534 B1 | 9/2001 | Hakamiun | |
| 6,428,099 B1 * | 8/2002 | Kain | B60N 2/2806 297/250.1 |
| 7,445,293 B2 | 11/2008 | Smith | |
| 8,322,788 B2 * | 12/2012 | Williams | B60N 2/2806 297/256.16 |
| 8,905,478 B2 * | 12/2014 | Strong | B60N 2/2806 297/250.1 |
| 9,150,126 B1 * | 10/2015 | Kitchens | B60N 2/2806 |
| 2017/0120783 A1 * | 5/2017 | Denbo | B60N 2/2884 |

* cited by examiner

*Primary Examiner* — Philip F Gabler

(57) ABSTRACT

The color-coded buckle straps for a wheelchair is an active restraint system. The color-coded buckle straps for a wheelchair is configured for use with a wheelchair. The color-coded buckle straps for a wheelchair secure a patient to the wheelchair. Each of the plurality of harnesses further comprises a buckle. Each buckle further comprises a male component and a female component. The buckle for each harness selected from the plurality of harnesses is selected such that the color of the buckle of any harness selected from the plurality of harnesses is different from the buckle of each unselected harness remaining within the plurality of harnesses. The color-coded buckle straps for a wheelchair comprises a chest harness, a waist harness, a pelvic harness, and a lower harness. The chest harness, the waist harness, the pelvic harness, and the lower harness are attached to the wheelchair.

20 Claims, 3 Drawing Sheets

COLOR-CODED BUCKLE STRAPS FOR A WHEELCHAIR

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

The present invention relates to the field of medical and veterinary science including the transportation and accommodation of patients, more specifically, a special provision for patients for transporting a patient in a wheelchair.

The requirement for mobility assistance for patients with ambulatory issues is a recurring problem within the medical community. The provisioning of this requirement can be complicated when a patient needs to be restrained for their own safety. An example for the need for restraint includes, but would not be limited to, a patient who: 1) presents a high probability for a fall risk; but, 2) does not recognize the severity of the risk. While effective restraint systems do exist to protect the patient, in many cases currently available circumstances when a caregiver is working alone and the patient is uncooperative.

A typical example of this shortcoming of current restraint systems occurs with a patient in: 1) a wheelchair; or, 2) another wheeled chair such as a stroller (hereinafter wheelchair). Typically, the wheelchair is staffed with a single care giver who is responsible both for the operation of the wheelchair and the safety of the patient in the wheelchair. Within this environment, to restrain a patient within the wheelchair the caregiver must: 1) maintain the position of the patient within the wheelchair; 2) place the patient within the restraint system associated with the wheelchair; 3) identify and match the male component with the female component for each buckle incorporated in the restraint system; and, 4) fasten the male component to the female component for each buckle incorporated in the restraint system. When a common buckle is used for the each buckle incorporated in the restraint system, the identification and fastening of the male component and female component of any specific buckle can be a time consuming and frustrating process—especially when care must be provided for a dynamic patient.

Clearly a method that visually and clearly identifies and incorporated in a restraint system would be of benefit to a caregiver.

SUMMARY OF INVENTION

The color-coded buckle straps for a wheelchair is an active restraint system that is adapted for use with a patient. The color-coded buckle straps for a wheelchair is configured for use with a vehicle selected from the group consisting of a wheelchair or a wheeled chair (hereinafter wheelchair). The color-coded buckle straps for a wheelchair comprises a plurality of harnesses that are integrated to secure the patient to the wheelchair. Each of the plurality of harnesses further comprises a buckle. Each buckle further comprises a male component and a female component. The buckle for each harness selected from the plurality of harnesses is selected such that: 1) with the exception of the color of the buckle, the buckle of any selected harness is identical to the buckle of every unselected harness remaining in the plurality of harnesses; 2) the color of the male component of the buckle of any selected harness matches the color of the female component; and, 3) the matched color of the male component and the female component of any selected harness visibly differs from the matched color of the male component and the female component of the buckle of every unselected harness remaining in the plurality of comprises a chest harness, a waist harness, a pelvic harness, and a lower harness. The chest harness, the waist harness, the pelvic harness, and the lower harness are attached to the wheelchair. The chest harness and the pelvic harness attach to each other.

These together with additional objects, features and advantages of the color-coded buckle straps for a wheelchair will be readily apparent to those of ordinary skill in the art upon reading the following detailed description of the presently preferred, but nonetheless illustrative, embodiments when taken in conjunction with the accompanying drawings.

In this respect, before explaining the current embodiments of the color-coded buckle straps for a wheelchair in detail, it is to be understood that the color-coded buckle straps for a wheelchair is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the color-coded buckle straps for a wheelchair.

It is therefore important that the claims be regarded as including such equivalent construction insofar as they do not straps for a wheelchair. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
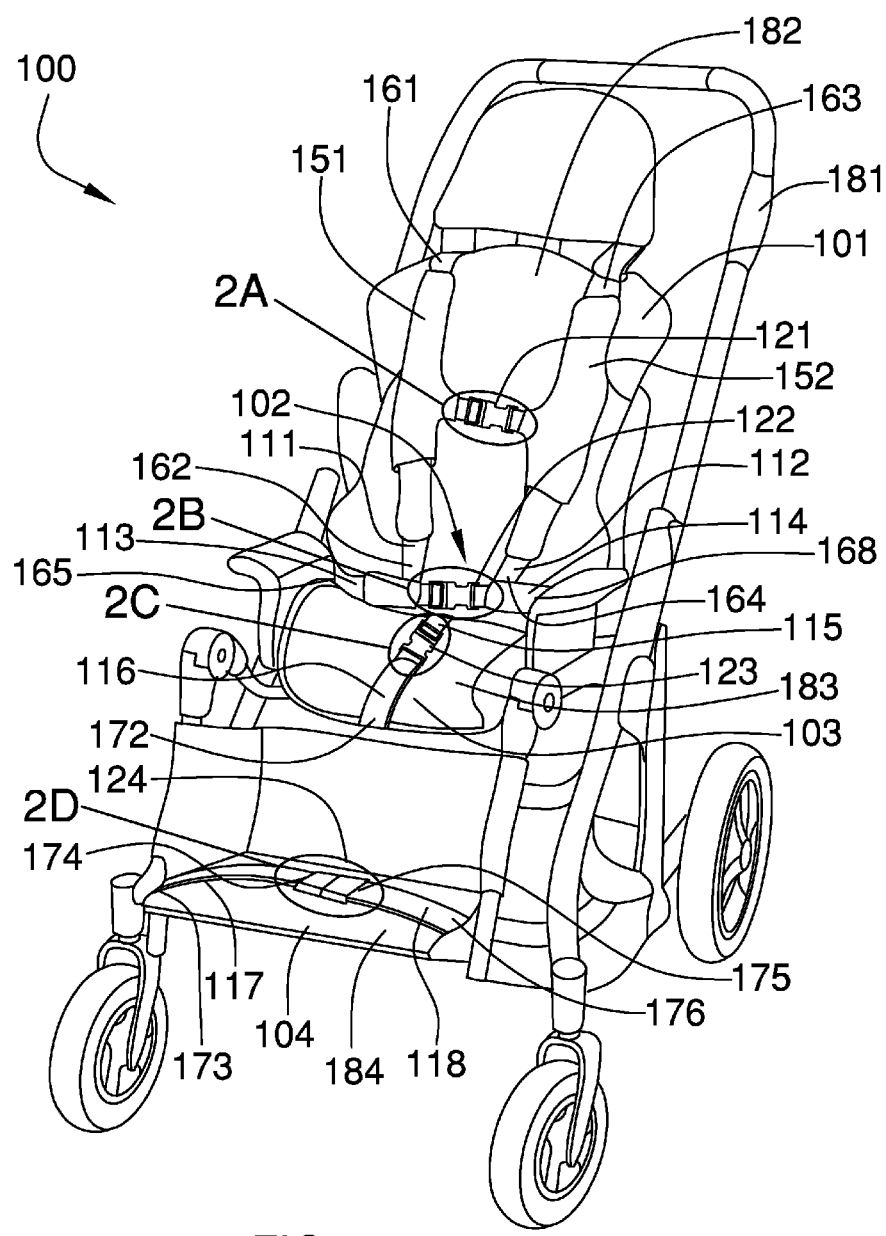
FIG. 1 is a perspective view of an embodiment of the disclosure.
Figure 2A:
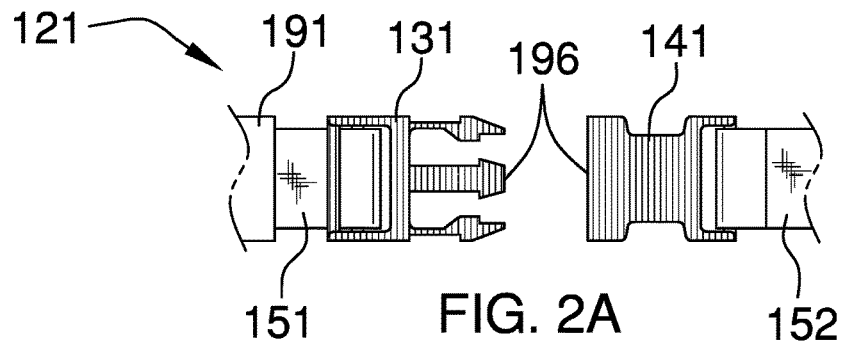
FIG. 2A is a detail view of an embodiment of the disclosure.
Figure 2B:
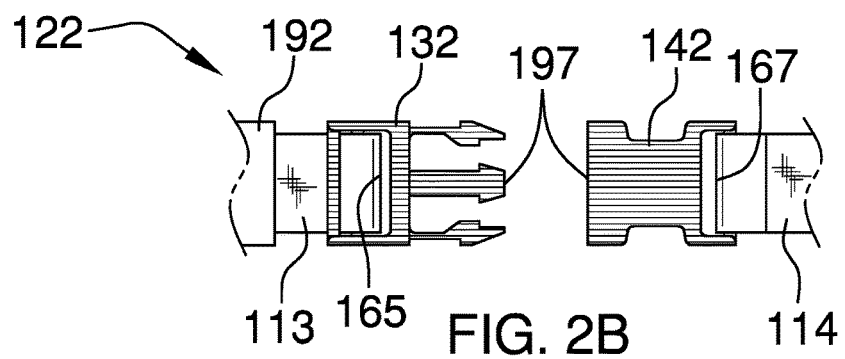
FIG. 2B is a detail view of an embodiment of the disclosure.
Figure 2C:
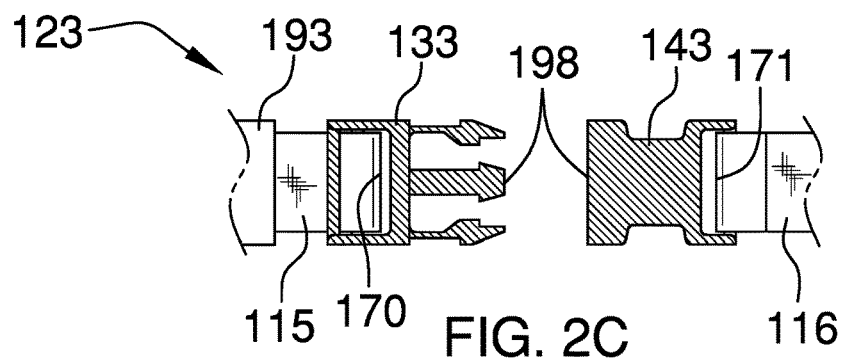
FIG. 2C is a detail view of an embodiment of the disclosure.
Figure 2D:
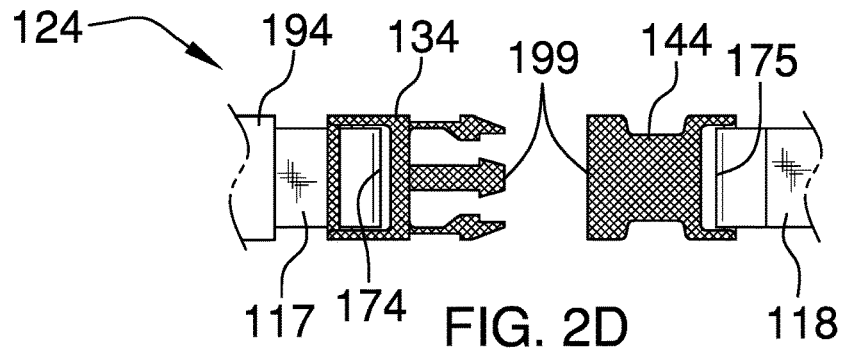
FIG. 2D is a detail view of an embodiment of the disclosure.
Figure 3:
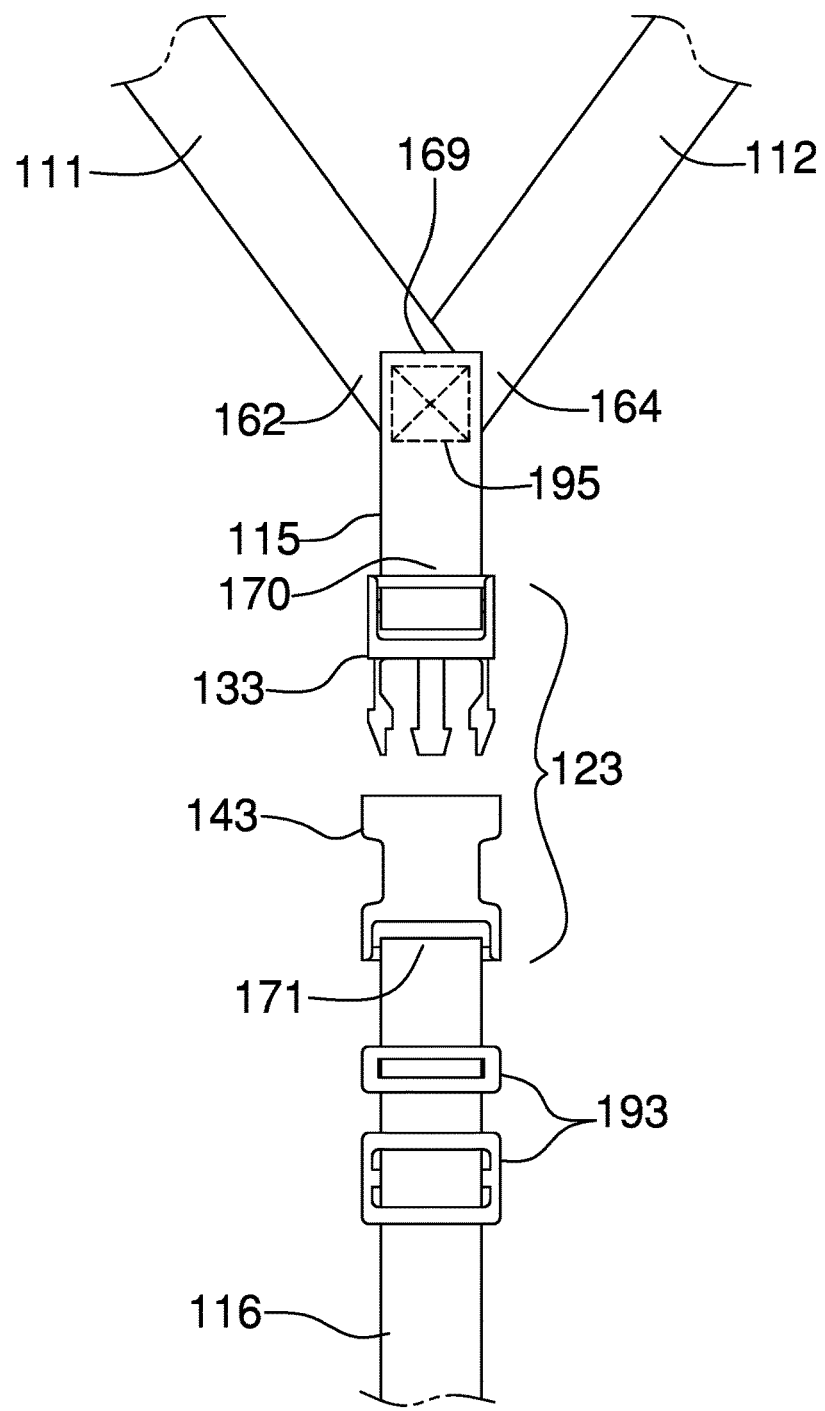
FIG. 3 is a detail view of an embodiment of the disclosure.

Detailed reference will now be made to one or more potential embodiments of the disclosure, which are illustrated in FIGS. 1 through 3.

The color-coded buckle straps for a wheelchair 100 (hereinafter invention) is an active restraint system that is adapted for use with a patient. The invention 100 is configured for use with a vehicle selected from the group consisting of a wheelchair 181 or a wheeled chair such as a stroller. Within wheelchair 181. The invention 100 comprises a plurality of harnesses that are integrated to secure the patient to the wheelchair 181. Each of the plurality of harnesses further comprises a buckle.

The wheelchair 181 is a wheeled vehicle that is used to transport a patient while in a seated position. The wheelchair 181 is further defined with a backrest 182, a seat 183, and a footplate 184. The backrest 182 forms a support for the back of the patient. The seat 183 is a bench upon which the patient sits. The footplate 184 is a shelf upon which the patient rests their feet.

Each buckle further comprises a male component and a female component. The buckle for each harness selected from the plurality of harnesses is selected such that: 1) with the exception of the color of the buckle, the buckle of any selected harness is identical to the buckle of every unselected harness remaining in the plurality of harnesses; 2) the color of the male component of the buckle of any selected harness matches the color of the female component; and, 3) the matched color of the male component and the female component of any selected harness visibly differs from the matched color of the male component and the female component of the buckle of every unselected harness remaining in the plurality of harnesses.

By matched is meant that the color difference between the male component and the female component of a matched buckle is less than 1.0 as measured using the CIELAB standard and methodology. By differs from the matched color is meant that the color difference between a first matched buckle and a second matched buckle is greater than 2.0 as measured using the CIELAB standard and methodology. The CIELAB defines a "color space" within which color differences between objects can be quantified. The CIELAB is well-known and documented within the textile, dyeing and spectrophotometry arts.

The plurality of harnesses comprises a chest harness, 101 a waist harness 102, a pelvic harness 103, and a lower harness 104. The chest harness 101, the waist harness 102, the pelvic harness 103, and the lower harness 104 are attached to the wheelchair 181. The chest harness 101 and the pelvic harness 103 attach to each other.

The chest harness 101 is the module of the invention 100 that secures the upper body of a patient to the wheelchair 181. The chest harness 101 forms a two point harness. The chest harness 101 comprises a first strap 111, a second strap 112, and a first quick release buckle 121.

The first strap 111 is a readily and commercially available textile webbing. The first strap 111 further comprises a first 152. The first strap 111 is further defined with a first end 161 and a second end 162. The second strap 112 is a readily and commercially available textile webbing. The second strap 112 is further defined with a third end 163 and a fourth end 164. The first pad 151 is a readily and commercially available shoulder pad configured for use as luggage straps. The second pad 152 is a readily and commercially available shoulder pad configured for use as luggage straps.

The first quick release buckle 121 is a readily and commercially available fastener commonly marketed as a quick release buckle with a ring and slider arrangement. The first quick release buckle 121 comprises a first male connector 131, a first female connector 141, and first ring and slider arrangement 191. The first male connector 131 is a male connector associated with the first quick release buckle 121. The first female connector 141 is a female connector associated with the first quick release buckle 121. The first ring and slider arrangement 191 is a well-known and documented device that is used to adjust the length of a strap or webbing.

The first quick release buckle 121 is further defined with a first color 196 such that both the color of the first male connector 131 and the color of the first female connector 141 match the first color 196. The first color 196 is a measurable person senses the distribution of the wavelengths of the electromagnetic radiation that reflects off of the first quick release buckle 121.

The waist harness 102 is the module of the invention 100 that secures the abdomen of a patient to the wheelchair 181. The waist harness 102 forms a two point harness.

The waist harness 102 comprises a third strap 113, a fourth strap 114, and a second quick release buckle 122.

The third strap 113 is a readily and commercially available textile webbing. The third strap 113 is further defined with a fifth end 165 and a sixth end 166. The fourth strap 114 is a readily and commercially available textile webbing. The fourth strap 114 is further defined with a seventh end 167 and an eighth end 168.

The second quick release buckle 122 is a readily and commercially available fastener commonly marketed as a quick release buckle with a ring and slider arrangement. The second quick release buckle 122 comprises a second male connector 132, a second female connector 142, and a second ring and slider arrangement 192. The second male connector 132 is a male connector associated with the second quick release buckle 122. The second female connector 142 is a female connector associated with the second quick release buckle 122. The second ring and slider arrangement 192 is a well-known and documented device that is used to adjust the length of a strap or webbing.

The second quick release buckle 122 is further defined with a second color 197 such that both the color of the second male connector 132 and the color of the second female connector 142 match the second color 197. The second color 197 is a property of the second quick release buckle 122 associated how a person senses the distribution of the wavelengths of the electromagnetic radiation that reflects off of the second quick release buckle 122. The color of the second color 197 differs from the color of the first color 196.

The pelvic harness 103 is the module of the invention 100 that secures the lower torso of the patient to the wheelchair 181. As shown most clearly in FIG. 3, the pelvic harness 103 forms a three point harness. The pelvic harness 103 comprises a fifth strap 115, a sixth strap 116, and a third quick release buckle 123.

The fifth strap 115 is a readily and commercially available textile webbing. The fifth strap 115 is further defined with a ninth end 169 and a tenth end 170. The sixth strap 116 is a readily and commercially available textile webbing. The sixth strap 116 is further defined with an eleventh end 171 and a twelfth end 172.

The third quick release buckle 123 is a readily and commercially available fastener commonly marketed as a quick release buckle with a ring and slider arrangement. The third quick release buckle 123 comprises a third male connector 133, a third female connector 143, and a third ring and slider arrangement 193. The third male connector 133 is a male connector associated with the third quick release buckle 123. The third female connector 143 is a female connector associated with the third quick release buckle 123. The third ring and slider arrangement 193 is a well-known and documented device that is used to adjust the length of a strap or webbing.

The third quick release buckle 123 is further defined with a third color 198 such that both the color of the third male connector 133 and the color of the third female connector 143 match the third color 198. The third color 198 is a property of the third quick release buckle 123 associated how a person senses the distribution of the wavelengths of the electromagnetic radiation that reflects off of the third quick release buckle 123. The color of the third color 198 differs from the colors of the first color 196 and the second color 197.

The lower harness 104 is the module of the invention 100 that secures the legs and feet of the patient to the wheelchair 181. The lower harness 104 forms a two point harness. The lower harness 104 comprises a seventh strap 117, an eighth strap 118, and a fourth quick release buckle 124.

The seventh strap 117 is further defined with a thirteenth end 173 and a fourteenth end 174. The eighth strap 118 is further defined with a fifteenth end 175 and a sixteenth end 176. The seventh strap 117 is a readily and commercially available textile webbing. The eighth strap 118 is a readily and commercially available textile webbing.

The fourth quick release buckle 124 is a readily and commercially available fastener commonly marketed as a quick release buckle with a ring and slider arrangement. The fourth quick release buckle 124 comprises a fourth male connector 134, a fourth female connector 144, and a fourth ring and slider arrangement 194. The fourth male connector 134 is a male connector associated with the fourth quick release buckle 124. The fourth female connector 144 is a female connector associated with the fourth quick release buckle 124. The fourth ring and slider arrangement 194 is a well-known and documented device that is used to adjust the length of a strap or webbing.

The fourth quick release buckle 124 is further defined with a fourth color 199 such that both the color of the fourth male connector 134 and the color of the fourth female connector 144 match the fourth color 199. The fourth color 199 is a property of the fourth quick release buckle 124 associated how a person senses the distribution of the wavelengths of the electromagnetic radiation that reflects off of the fourth quick release buckle 124. The color of the fourth color 199 differs from the colors of the first color 196, the second color 197, and the third color 198.

As shown most clearly in FIG. 1, the invention 100 is installed in a wheelchair 181 as described in following three paragraphs.

The first end 161 of the first strap 111 is anchored to the superior edge of the backrest 182 of the wheelchair 181. The third end 163 of the second strap 112 is anchored to the superior edge of the backrest 182 of the wheelchair 181. The first strap 111 is threaded through the first pad 151. The second strap 112 is threaded through the second pad 152. The first male connector 131 and the first ring and slider arrangement 191 of the first quick release buckle 121 is attached to the first pad 151. The first female connector 141 of the first quick release buckle 121 is attached to the second pad 152. The second end 162 of the first strap 111 and the fourth end 164 of the second strap 112 both attach to the ninth end 169 of the fifth strap 115 using a sewn seam 195.

The fifth end 165 of the third strap 113 is anchored to the seat 183 of the wheelchair 181. The eighth end 168 of the fourth strap 114 is anchored to the seat 183 of the wheelchair 181. The twelfth end 172 of the sixth strap 116 is anchored to the seat 183 of the wheelchair 181. The thirteenth end 173 of the seventh strap 117 is anchored to the footplate 184 of the wheelchair 181. The sixteenth end 176 of the eighth strap 118 is anchored to the footplate 184 of the wheelchair 181.

The second male connector 132 and the second ring and slider arrangement 192 of the second quick release buckle 122 is attached to the sixth end 166 of the third strap 113. The second female connector 142 of the second quick release buckle 122 is attached to the seventh end 167 of the fourth strap 114. The third male connector 133 and the third ring and slider arrangement 193 of the third quick release buckle 123 is attached to the tenth end 170 of the fifth strap 115. The third female connector 143 of the third quick release buckle 123 is attached to the eleventh end 171 of the sixth strap 116. The fourth male connector 134 and the fourth ring and slider arrangement 194 of the fourth quick release buckle 124 is attached to the fourteenth end 174 of the seventh strap 117. The fourth female connector 144 of the fourth quick release buckle 124 is attached to the fifteenth end 175 of the eighth strap 118.

The procedure to secure a patient in the invention 100 is described in the following two paragraphs paragraph.

The patient is placed in the wheelchair 181. The first strap 111 is placed over the right shoulder of the patient. The second strap 112 is placed over the left shoulder of the patient. The first male connector 131 of the first quick release buckle 121 is inserted into the first female connector 141 of the first quick release buckle 121. The third strap 113 is placed over the waist of the patient. The fourth strap 114 is placed over the waist of the patient. The second male connector 132 of the second quick release buckle 122 is inserted into the second female connector 142 of the second quick release buckle 122.

The third male connector 133 of the third quick release buckle 123 is inserted into the third female connector 143 of the third quick release buckle 123. The seventh strap 117 is placed over the feet of the patient. The eighth strap 118 is placed over the feet of the patient. The fourth male connector 134 of the fourth quick release buckle 124 is inserted into the fourth female connector 144 of the fourth quick release buckle 124. The first ring and slider arrangement 191, the second ring and slider arrangement 192, the third ring and slider arrangement 193, and the fourth ring and slider arrangement 194 are individually adjusted to customize the fit of the invention 100 to the patient.

The differences between the first color 196, the second color 197, the third color 198, and the fourth color 199 are used to visibly identify and match for fastening purposes the first quick release buckle 121, the second quick release buckle 122, the third quick release buckle 123 and the fourth quick release buckle 124.

The following definitions were used in this disclosure:

Anchor: As used in this disclosure, anchor means to hold an object firmly or securely.

Anchor Point: As used in this disclosure, an anchor point is a location to which a first object can be securely attached to a second object.

Buckle: As used in this disclosure, a buckle is a fastening that is used for joining a first loose end of a strap to a second loose end of the same strap or a different strap. A buckle further comprises a male connector that is attached to a first loose end and a female connector that is attached to a second loose end. The male connector has a pin or other structure that is generally caught by a structure formed in the female connector.

CIE: As used in this disclosure, the CIE is an acronym for the International Commission on Illumination.

CIELAB: As used in this disclosure, the CIELAB is a color space coordinate system that is used to specify color. The CIELAB is a system that is defined and maintained by the International Commission on Illumination. At the time of this disclosure, the current CIELAB is referred to as CIELAB2000.

Cushion: As used in this disclosure a cushion is a structure formed from a pad that is used to prevent injury or damage to a person or object.

Fastener: As used in this disclosure, a fastener is a device that is used to join or affix two objects. Fasteners generally comprise a first element which is attached to the first object and a second element which is attached to the second object such that the first element and the second element join to affix the first object and the second object. Common fasteners include, but are not limited to, hooks, zippers, snaps, buttons, buckles, quick release buckles, or hook and loop fasteners.

Harness: As used in this disclosure, a harness is an apparatus comprising a plurality of straps and one or more fasteners that is used to fasten or anchor a first person or first object to a second object. The phrase N point harness refers to the installation of the harness wherein the harness has N anchor points. For example, a 2 point harness has two anchor points while a 5 point harness has 5 anchor points.

Inferior: As used in this disclosure, the term inferior refers to a directional reference that is parallel to and in the same direction as the force of gravity.

Pad: As used in this disclosure, a pad is a mass of soft material used as a filling or for protection against damage or injury. Commonly used padding materials include, but are not limited to, polyurethane foam, a polyester fill often referred to as fiberfill or polystyrene beads often referred to as stuffing beans or as bean bag chair beans.

Patient: As used in this disclosure, a patient is a person who is designated to receive a medical treatment, therapy or service. The term patient may be extended to an animal when used within the context of the animal receiving veterinary treatment or services Quick Release Buckle: As used in this disclosure, a quick release buckle is a specific type of buckle wherein the buckle can be readily and easily disconnected by pressing a button or pinching one of the ends of the quick release buckle. Quick release buckles are readily and commercially available.

Ring and Slider Arrangement: As used in this disclosure, a ring and slider arrangement is an apparatus comprising a ring component and a slider component that is used to adjust the effective length of a webbing in an application. In the ring and slider arrangement, an end of the webbing is inserted through the slider component, looped through the ring component and then reverse threaded through the slider component for a second time. By adjusting the position of the slider component relative to the webbing, the effective length of the webbing can be adjusted. Ring and slider arrangements are well known and documented in the textile arts.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Superior: As used in this disclosure, the term superior refers to a directional reference that is parallel to and in the opposite direction of the force of gravity.

Textile: As used in this disclosure, a textile is a material that is woven, knitted, braided or felted. Synonyms in common usage for this definition include fabric and cloth.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips.

Wheelchair: As used in this disclosure, a wheelchair is a chair fitted with four wheels that is used for transporting a patient. The wheelchair is commonly used for sick or disabled persons. Within this disclosure, the common definition of wheelchair is extended to include a stroller.

With respect to the above description, it is to be realized that the optimum dimensional relationship for the various components of the invention described above and in FIGS. 1 through 3 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A restraint system comprising:
a plurality of harnesses;
wherein each of the plurality of harnesses further comprises a buckle;
wherein each buckle further comprises a male component and a female component;

wherein the male component inserts into the female component to fasten the buckle;
wherein the restraint system is an active restraint system;
wherein the restraint system is configured for use with a vehicle selected from the group consisting of a wheelchair or a wheeled chair;
wherein the selected vehicle is further defined with a backrest, a seat, and a footplate;
wherein the buckle for each harness selected from the plurality of harnesses is selected such that, with the exception of the color of the buckle, the buckle of any selected harness is identical to the buckle of every unselected harness remaining in the plurality of harnesses;
wherein the buckle for each harness selected from the plurality of harnesses is selected such that the color of the male component of the buckle of any selected harness matches the color of the female component;
wherein the buckle for each harness selected from the plurality of harnesses is selected such that the matched color of the male component and the female component of any selected harness visibly differs from the matched color of the male component and the female component of the buckle of every unselected harness remaining in the plurality of harnesses.

2. The restraint system according to claim 1
wherein the plurality of harnesses comprises a chest harness, a waist harness, a pelvic harness, and a lower harness;
wherein the chest harness, the waist harness, the pelvic harness, and the lower harness are configured to be attached to the selected vehicle;
wherein the chest harness and the pelvic harness attach to each other.

3. The restraint system according to claim 2
wherein the chest harness forms a two point harness;
wherein the chest harness comprises a first strap, a second strap, and a first quick release buckle;
wherein the first quick release buckle attaches the first strap to the second strap.

4. The restraint system according to claim 3
wherein the first quick release buckle is a fastener;
wherein the first quick release buckle comprises a first male connector, a first female connector, and first ring and slider arrangement;
wherein the first male connector is the male connector associated with the first quick release buckle;
wherein the first female connector is the female connector associated with the first quick release buckle;
wherein the first ring and slider arrangement is a device that is used to adjust the length of a webbing;
wherein the first quick release buckle is further defined with a first color such that both the color of the first male connector and the color of the first female connector match the first color;
wherein the first color is a property of the first quick release buckle associated with the distribution of the wavelengths of the electromagnetic radiation that reflects off of the first quick release buckle.

5. The restraint system according to claim 4
wherein the waist harness forms a two point harness;
wherein the waist harness comprises a third strap, a fourth strap, and a second quick release buckle;
wherein the second quick release buckle attaches the third strap to the fourth strap.

6. The restraint system according to claim 5
wherein the second quick release buckle comprises a second male connector, a second female connector, and a second ring and slider arrangement;
wherein the second male connector is a male connector associated with the second quick release buckle;
wherein the second female connector is a female connector associated with the second quick release buckle;
wherein the second ring and slider arrangement is a device that is used to adjust the length of a webbing;
wherein the second quick release buckle is further defined with a second color such that both the color of the second male connector and the color of the second female connector match the second color;
wherein the second color is a property of the second quick release buckle associated with the distribution of the wavelengths of the electromagnetic radiation that reflects off of the second quick release buckle.

7. The restraint system according to claim 6 wherein the color of the second color differs from the color of the first color.

8. The restraint system according to claim 7
wherein the pelvic harness forms a three point harness;
wherein the pelvic harness comprises a fifth strap, a sixth strap, and a third quick release buckle;
wherein the third quick release buckle attaches the fifth strap to the sixth strap.

9. The restraint system according to claim 8
wherein the third quick release buckle comprises a third male connector, a third female connector, and a third ring and slider arrangement;
wherein the third male connector is a male connector associated with the third quick release buckle;
wherein the third female connector is a female connector associated with the third quick release buckle;
wherein the third ring and slider arrangement is a device that is used to adjust the length of webbing;
wherein the third quick release buckle is further defined with a third color such that both the color of the third male connector and the color of the third female connector match the third color;
wherein the third color is a property of the third quick release buckle associated how a person senses the distribution of the wavelengths of the electromagnetic radiation that reflects off of the third quick release buckle.

10. The restraint system according to claim 9 wherein the color of the third color differs from the colors of the first color and the second color.

11. The restraint system according to claim 10
wherein the lower harness forms a two point harness;
wherein the lower harness comprises a seventh strap, an eighth strap, and a fourth quick release buckle;
wherein the fourth quick release buckle attaches the seventh strap to the eighth strap.

12. The restraint system according to claim 11
wherein the fourth quick release buckle comprises a fourth male connector, a fourth female connector, and a fourth ring and slider arrangement;
wherein the fourth male connector is a male connector associated with the fourth quick release buckle;
wherein the fourth female connector is a female connector associated with the fourth quick release buckle;
wherein the fourth ring and slider arrangement is a device that is used to adjust the length of a strap or webbing;
wherein the fourth quick release buckle is further defined with a fourth color such that both the color of the fourth male connector and the color of the fourth female connector match the fourth color;

wherein the fourth color is a property of the fourth quick release buckle associated how a person senses the distribution of the wavelengths of the electromagnetic radiation that reflects off of the fourth quick release buckle.

13. The restraint system according to claim 12 wherein the color of the fourth color differs from the colors of the first color, the second color, and the third color.

14. The restraint system according to claim 13
wherein the first strap further comprises a first pad;
wherein the second strap further comprises a second pad;
wherein the first pad is a shoulder pad;
wherein the second pad is a shoulder pad.

15. The restraint system according to claim 14
wherein the first strap is a textile webbing;
wherein the first strap is further defined with a first end and a second end;
wherein the second strap is a textile webbing;
wherein the second strap is further defined with a third end and a fourth end.

16. The restraint system according to claim 15
wherein the third strap is a textile webbing;
wherein the third strap is further defined with a fifth end and a sixth end;
wherein the fourth strap is a textile webbing;
wherein the fourth strap is further defined with a seventh end and an eighth end.

17. The restraint system according to claim 16
wherein the fifth strap is a textile webbing;
wherein the fifth strap is further defined with a ninth end and a tenth end;
wherein the sixth strap is a textile webbing;
wherein the sixth strap is further defined with an eleventh end and a twelfth end.

18. The restraint system according to claim 17
wherein the seventh strap is further defined with a thirteenth end and a fourteenth end;
wherein the eighth strap is further defined with a fifteenth end and a sixteenth end;
wherein the seventh strap is a readily and commercially available textile webbing;
wherein the eighth strap is a readily and commercially available textile webbing.

19. The restraint system according to claim 18
wherein the first end of the first strap is configured to be anchored to the superior edge of the backrest of the selected vehicle;
wherein the third end of the second strap is configured to be anchored to the superior edge of the backrest of the selected vehicle;
wherein the first strap is threaded through the first pad;
wherein the second strap is threaded through the second pad;
wherein the first male connector and the first ring and slider arrangement of the first quick release buckle is attached to the first pad;

wherein the first female connector of the first quick release buckle is attached to the second pad;
wherein the second end of the first strap and the fourth end of the second strap both attach to the ninth end of the fifth strap using a sewn seam;
wherein the fifth end of the third strap is configured to be anchored to the seat of the selected vehicle;
wherein the eighth end of the fourth strap is configured to be anchored to the seat of the selected vehicle;
wherein the twelfth end of the sixth strap is configured to be anchored to the seat of the selected vehicle;
wherein the thirteenth end of the seventh strap is configured to be anchored to the footplate of the selected vehicle;
wherein the sixteenth end of the eighth strap is configured to be anchored to the footplate of the selected vehicle;
wherein the second male connector and the second ring and slider arrangement of the second quick release buckle is attached to the sixth end of the third strap;
wherein the second female connector of the second quick release buckle is attached to the seventh end of the fourth strap;
wherein the third male connector and the third ring and slider arrangement of the third quick release buckle is attached to the tenth end of the fifth strap;
wherein the third female connector of the third quick release buckle is attached to the eleventh end of the sixth strap;
wherein the fourth male connector and the fourth ring and slider arrangement of the fourth quick release buckle is attached to the fourteenth end of the seventh strap;
wherein the fourth female connector of the fourth quick release buckle is attached to the fifteenth end of the eighth strap.

20. The restraint system according to claim 19
wherein the first male connector of the first quick release buckle is inserted into the first female connector of the first quick release buckle;
wherein the second male connector of the second quick release buckle is inserted into the second female connector of the second quick release buckle;
wherein the third male connector of the third quick release buckle is inserted into the third female connector of the third quick release buckle;
wherein the fourth male connector of the fourth quick release buckle is inserted into the fourth female connector of the fourth quick release buckle;
wherein the first ring and slider arrangement, the second ring and slider arrangement, the third ring and slider arrangement, and the fourth ring and slider arrangement are individually adjusted to customize the fit of the restraint system;
wherein the differences between the first color, the second color, the third color, and the fourth color are used to visibly identify and match for fastening purposes the first quick release buckle, the second quick release buckle, the third quick release buckle and the fourth quick release buckle.

* * * * *